(12) United States Patent
Dimitrova et al.

(10) Patent No.: US 8,357,112 B2
(45) Date of Patent: Jan. 22, 2013

(54) METHOD OF CONTROLLING A RELEASE OF A MATERIAL CARRIED BY ULTRASOUND SENSITIVE PARTICLES

(75) Inventors: Nevenka Dimitrova, Pelham Manor, NY (US); Christopher S. Hall, Hopewell Junction, NY (US); Chien T. Chin, Tarrytown, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 595 days.

(21) Appl. No.: 12/530,243

(22) PCT Filed: Mar. 3, 2008

(86) PCT No.: PCT/IB2008/050763
§ 371 (c)(1),
(2), (4) Date: Sep. 8, 2009

(87) PCT Pub. No.: WO2008/110958
PCT Pub. Date: Sep. 18, 2008

(65) Prior Publication Data
US 2010/0106078 A1   Apr. 29, 2010

Related U.S. Application Data

(60) Provisional application No. 60/893,916, filed on Mar. 9, 2007.

(51) Int. Cl.
*A61B 17/20* (2006.01)
(52) U.S. Cl. ............ 604/22; 604/522; 600/437
(58) Field of Classification Search .......... 604/22, 604/48, 500, 522; 600/439, 437
See application file for complete search history.

(56) References Cited

U.S. PATENT DOCUMENTS

| 5,190,766 A | 3/1993 | Ishihara |
| 5,542,935 A | 8/1996 | Unger |
| 6,176,842 B1 | 1/2001 | Tachibana |
| 6,740,039 B1 * | 5/2004 | Rafter et al. ............ 600/439 |
| 6,896,659 B2 * | 5/2005 | Conston et al. ........... 600/458 |
| 2002/0151792 A1 | 10/2002 | Conston |

(Continued)

FOREIGN PATENT DOCUMENTS

WO   0012062 A1   3/2000

(Continued)

OTHER PUBLICATIONS

Bekeredjian, Raffi et al "Use of Ultrasound Contrast Agents for Gene or Drug Delivery in Cardiovascular Medicine" Journal of the American College of Cardiology 2005, vol. 45, No. 3, pp. 329-335.

(Continued)

*Primary Examiner* — Kevin C Sirmons
*Assistant Examiner* — Deanna K Hall (57) ABSTRACT

This invention relates to a method and an apparatus of controlling a release of a material carried by ultrasound sensitive particles, the release being caused by irradiating the ultrasound sensitive particles with an ultrasonic pulse having acoustic properties selected so as to interact with the ultrasound sensitive particles and thus causing the release of the material. The ultrasound sensitive particles comprise subgroups of ultrasound sensitive particles, the ultrasound sensitive particles within the same sub-group having their respective acoustic property causing each respective subgroup to interact independently with the sound wave.

20 Claims, 6 Drawing Sheets

U.S. PATENT DOCUMENTS

| | | |
|---|---|---|
| 2003/0039613 A1 | 2/2003 | Unger |
| 2003/0147812 A1 | 8/2003 | Ueberle |
| 2004/0059219 A1 | 3/2004 | Asafusa |
| 2004/0229830 A1 | 11/2004 | Tachibana |

FOREIGN PATENT DOCUMENTS

| | | |
|---|---|---|
| WO | 0112069 A1 | 2/2001 |
| WO | 2004060447 A2 | 7/2004 |

OTHER PUBLICATIONS

Rome, Claire et al "Spatial and Temporal Control of Expression of Therapeutic Genes using Heat Shock Protein Promotors" Methods, vol. 35, No. 2, 2005, pp. 188-198.

Shi, William et al "Ultrasonic Characterization of Novel Monodispersed Contrast Agents" Proceedings of 2006 IEEE Ultrasonics Symposium, pp. 301-304.

* cited by examiner

METHOD OF CONTROLLING A RELEASE OF A MATERIAL CARRIED BY ULTRASOUND SENSITIVE PARTICLES

FIELD OF THE INVENTION

The present invention relates to a method and an apparatus for controlling a release of a material carried by ultrasound sensitive particles.

BACKGROUND OF THE INVENTION

Ultrasound provides a unique opportunity to deposit energy remotely into inaccessible human tissue for therapeutic purposes. In the past, such approaches have used one of two mechanisms to activate therapeutic interventions. Ultrasonically deposited energy can be manifested through heat for the activation of heat shock proteins (C. Rome, F. Couillaud and C. T. W. Moonen, *Spatial and temporal control of expression of therapeutic genes using shock protein promoters*. Methods, 2005. 35(2): p. 188-198), or other temperature sensitive therapies. In addition, ultrasound sensitive particles administered through intra-venous or arterial injection can be used through the incorporation of specific pharmaceutical or genetic material into the particle or on particle shell and the remote activation through the use of specially designed single ultrasound pulses (R. Bekeredjian, P. A. Grayburn, and R. V. Shohet, *Use of ultrasound contrast agents for gene or drug delivery in cardiovascular medicine*, Journal of the American College of Cardiology, 2005. 45(3): p. 329-335).

Typical ultrasound sensitive particles consist of stabilized microbubbles. These microbubbles are usually less than 5 microns in diameter, stabilized with a shell consisting of protein, lipid, and/or polymers, with gaseous interior. These microbubbles possess the ability to interact with the ultrasound field through resonant behavior within the typical diagnostic imaging frequency range. The resonant behavior can be used to drive the bubbles from a resonant regime where the motion of the bubble is stable to a regime where the bubble expands and collapses violently and transiently. In both cases, it has been observed that when the bubbles incorporate genetic and pharmaceutical material on, within or even in close proximity to the bubble, it is possible to deliver the material to the surrounding tissue using ultrasound.

These prior art methods however suffer from the difficulty that it is impossible to control the rate of release of a material carried by the microbubbles and the spatial location of the released material. As an example, it might be required to deliver material A to a particular tissue, and subsequently material B. Such an operation is not possible with the existing technique. Further, when using ultrasound-mediated gene delivery techniques in vivo or in cell culture, in the past it has not always possible to visualize the presence and the execution of specific instruction sets and the specified outcome of this instruction set.

BRIEF DESCRIPTION OF THE INVENTION

An object of the present invention is to provide a method and an apparatus that enables to select the type of the material to be released. Advantageously, the rate of the release and the spatial location of the release is controlled.

According to one aspect, the present invention relates to a method of controlling a release of a material carried by ultrasound sensitive particles, the release being caused by irradiating the ultrasound sensitive particles with an ultrasonic pulse having acoustic properties selected so as to interact with the ultrasound sensitive particles and thus causing the release of the material, wherein the ultrasound sensitive particles comprise sub-groups of ultrasound sensitive particles, the ultrasound sensitive particles within the same sub-group having their respective acoustic property causing each respective sub-group to interact independently with the ultrasonic pulse.

Since the ultrasound sensitive particles comprise sub-groups having different acoustic properties, it is possible to let the ultrasound sensitive particles to act in a "programmed manner", or as a basic Turing machine. Accordingly, the sub-groups of the particles correspond to "data instances" that can be acted upon with ultrasound at a specific frequency or frequencies, amplitude, and other parameters, to enact a computing step. This means that the particles within the same sub-group can be activated and thus the material carried by the particles can be released based on the acoustic property of the ultrasonic pulse, while the other sub-groups are not activated. Accordingly, by changing the acoustic property of the ultrasonic pulse the type of material to be released can be changed. The ultrasound can accordingly be used to control the delivery of the material. In the analogy to a computing system, ultrasound acts as the memory controller fetching "instructions", i.e. delivering ultrasound with specific acoustic properties to cause activation i.e. data processing, where data is the biological/genetic material.

In one embodiment, the ultrasound sensitive particles within the same sub-group of ultrasound sensitive particles carry the same type of material.

Thus, the release of a specific material can be controlled accurately, e.g. by releasing the material in sub-group A, or first releasing the material in sub-group A and subsequently the material in sub-group B.

In one embodiment, the sub-groups of ultrasound sensitive particles comprise microbubbles containing the material therein.

It is an advantage to use such microbubbles since they can be selectively activated with judicious choice of properties of the ultrasound field.

In another embodiment, the sub-groups of ultrasound sensitive particles comprise microbubbles having a shell structure containing the material therein.

The shell structure can be made with extremely narrow size distribution which e.g. resonates over a narrow frequency range. Thus, by using such microbubbles having such shell structure, it is possible to produce many sub-groups of microbubbles that have different acoustic properties, e.g. different resonance frequencies.

In one embodiment, the shell structure within the same sub-group has similar physical property, the property being characteristic for the respective acoustic activation property.

Thus, the property of the ultrasonic pulse may be selected such that it interacts only with a particular group at a time.

In one embodiment, the physical property is selected from:
the shell thickness,
the shell size,
the diameter of the shell,
geometrical shape of the shell,
the number density of particles,
over or under filling of the gas in the bubbles,
the quantity of therapeutic or inert material relative to the number of bubbles,
chemical composition of the shell and
a combination thereof.

In one embodiment, the sub-groups of ultrasound sensitive particles are selected from:
- microbubbles having a shell structure containing said type of material therein,
- microbubbles containing said type of material therein
- microbubbles in a solution containing the type of material therein
- nanoparticles,
- liposomes,
- heat shock proteins, and
- a combination thereof.

In one embodiment, the material carried by ultrasound sensitive particles is a biological material and is selected from:
- pharmaceutical material,
- polysaccharides,
- lipids,
- fatty acids,
- steroids,
- proteins,
- enzymes,
- deoxyribonucleic acid (DNA),
- ribonucleic acid (RNA),
- small interfering ribonucleic acid (siRNA),
- inorganic artificial constructs,
- nanoparticles
- nanomachines,
- chemicals intended to alter the composition or geometry of existing sub-groups of particles,
- biochemical particles, and
- a combination thereof.

In one embodiment, the respective acoustic activation property of the ultrasound sensitive particles within the same sub-group is a common resonance frequency or resonance frequency range.

In one embodiment, the acoustic properties of the sound wave are selected from:
- a frequency corresponding to the resonance frequency of the one or more of the sub-groups,
- the pressure amplitude of the ultrasonic pulse,
- the duration of the ultrasonic pulse,
- an arbitrary waveform, and
- a combination thereof.

In one embodiment, the release of the material is carried out locally in or nearby a target tissue or cell by releasing the material from at least one of the sub-groups of the ultrasound sensitive particles.

Thus, it is possible to deliver the material, or pre-defined combination of the materials, directly into e.g. the tissue, e.g. by first releasing material A carried by e.g. sub-group a, into the tissue and subsequently material B carried by e.g. sub-group b.

Thus different possibilities exist to activate the ultrasound sensitive particles for causing the release of the material. As an example, if the ultrasound sensitive particles are microbubbles having shell structure, the shell structure may be made such that the microbubbles resonate over a narrow frequency range and are susceptible to rupture at a sharp pressure threshold.

In one embodiment, the method is performed in-vivo or in cell culture, the method further comprising:
- receiving a program comprising at least one command indicating at least one spatial delivery zone, each command indicating at least one type of material to be released at specific ratios,
- imaging the spatial distribution of the ultrasound sensitive particles, the imaging resulting in data indicting the spatial distribution of the ultrasound sensitive particles, and in response to the spatial data
- irradiating the ultrasound sensitive particles in the at least one delivery zone with an ultrasonic pulse, the property of the ultrasonic pulse being controlled such that the release of the material in the at least one delivery zone is in accordance to the at least one received command,
- repeating steps b)-c) for each subsequent command until the received commands have been completed.

By imaging the spatial distribution of the ultrasound sensitive particles it is possible to detect the presence of the various sub-groups in the intended spatial deliver zone. If as an example at a particular delivery zone, e.g. a cell or a tissue, the material C carried by sub-group c was supposed to be delivered to the particular delivery zone, but the imaging shows that there are excessive ultrasound sensitive particles belonging to sub-group c left, the irradiation will be made to continue until the imaging shows that the specified amount of sub-group c is released. Thus, an iteration process is provided that ensures a precise delivery of the material. Since the ultrasound sensitive particles within the various sub-groups may be considered as a set of "instructions", e.g. ultrasound sensitive particles within the same group carry the same set of instructions, this iteration may be considered as a method to monitor step by step the execution of the "instructions".

In one embodiment, the commands further include information about the amount of material to be delivered at a given delivery zone or the mix of material to be delivered at a given delivery zone or the material to be released in order to modify the acoustic properties of the remaining ultrasound sensitive particles.

Thus, the commands may e.g. comprise that only half of the ultrasound sensitive particles within group c are to be delivered at a given delivery zone. Further, the commands may include subsequently releasing another type of material in the same delivery zone.

The commands can be interpreted as equivalent to an "assignment" statement in a programming language: e.g. A=b. According to the invention, the particles may be floating and the material carried by the particles is not yet released. When such a simple command is issued the ultrasonic pulse induces the release of the material. Therefore, the material can be considered to be absorbed into the tissue/environment (similar to an assignment statement—the tissue "gets" a new value.

The commands may be 'conditional' meaning that there is an evaluative command, i.e. an "if" condition, and only when this is true there is execution of an ultrasonic pulse to activate e.g. A particles, otherwise, based on a readout, the system executes a B command, activates B particles.

The commands may also be 'looping' meaning to denote that a command will be executed, or a set of commands such as assignment or conditional or other looping commands, while a condition holds true, based on a readout/imaging.

According to another aspect the present invention relates to an apparatus for controlling a release of a material carried by ultrasound sensitive particles, comprising:
- a control unit, adapted to release a control signal,
- an ultrasound transducer adapted to be coupled to the control unit for irradiating, in response to the control signal from the control unit, the ultrasound sensitive particles with an ultrasonic pulse having acoustic properties selected so as to interact with the ultrasound sensitive particles and thus causing the release of the material, wherein the ultrasound sensitive particles comprise sub-groups of ultrasound sensitive particles each of the sub-groups having their respective acoustic property, the ultrasound transducer being adapted to irradiate the ultrasound sensitive particles with ultrasonic pulse having the acoustic properties of the sub-groups.

Thus, an apparatus is provided where allows the release of a material to be performed in a controlled manner, or in a "programmed" manner.

In one embodiment, the apparatus further comprises input means for receiving instructions indicating at least one spatial delivery zone and the type of material to be released at the at least one spatial delivery zone.

Thus, in case the instructions, which e.g. may be simple commands, conditional and looping commands, are manual instruction the operator of the apparatus can manually enter the desired locations where the material is to be released and the amount or combination of material to be released at the different spatial locations. In case the instructions are specified via a software code, a highly advanced way is provided for controlling the release of the material, where a full control is provided over the spatial locations as well as the amount and/or the mixing of the various materials at certain locations. By instructing per defined grammar is meant a pre-specified manner in which the programming constructs can be combined into a legal "program".

In one embodiment, the apparatus further comprises:

an imaging means coupled to the control unit for imaging the spatial distribution of the ultrasound sensitive particles, the imaging resulting in data indicting the spatial distribution of the ultrasound sensitive particles, wherein in response to the spatial data the control unit instructs the ultrasound transducer to irradiate the ultrasound sensitive particles localized nearby the at least one spatial delivery zone with an ultrasonic pulse, the property of the ultrasonic pulse being controlled such that the release of the material at the at least one spatial delivery zone is in accordance to the instructions accordance to the received instructions.

Thus, the ultrasound sensitive particles having the same acoustic property can be considered as abstract instruction units that interact simultaneously to the same ultrasonic pulse of a particular acoustic property.

According to still another aspect, the present invention relates to ultrasound sensitive particles comprising sub-groups of ultrasound sensitive particles carrying material, the ultrasound sensitive particles within the same sub-group having their respective acoustic property.

In one embodiment, the diameter of the ultrasound sensitive particles is less than 100 nm, such as less than 50 nm, such as less than 25 nm, such as less than 10 nm, such as less than 5 nm.

However, for certain applications it might be preferred to use particles having larger diameters.

In one embodiment, the particles within the same group carry the same type of material.

According to yet another aspect, the present invention relates to a use of ultrasound sensitive particles for delivering the material into cells or tissues.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
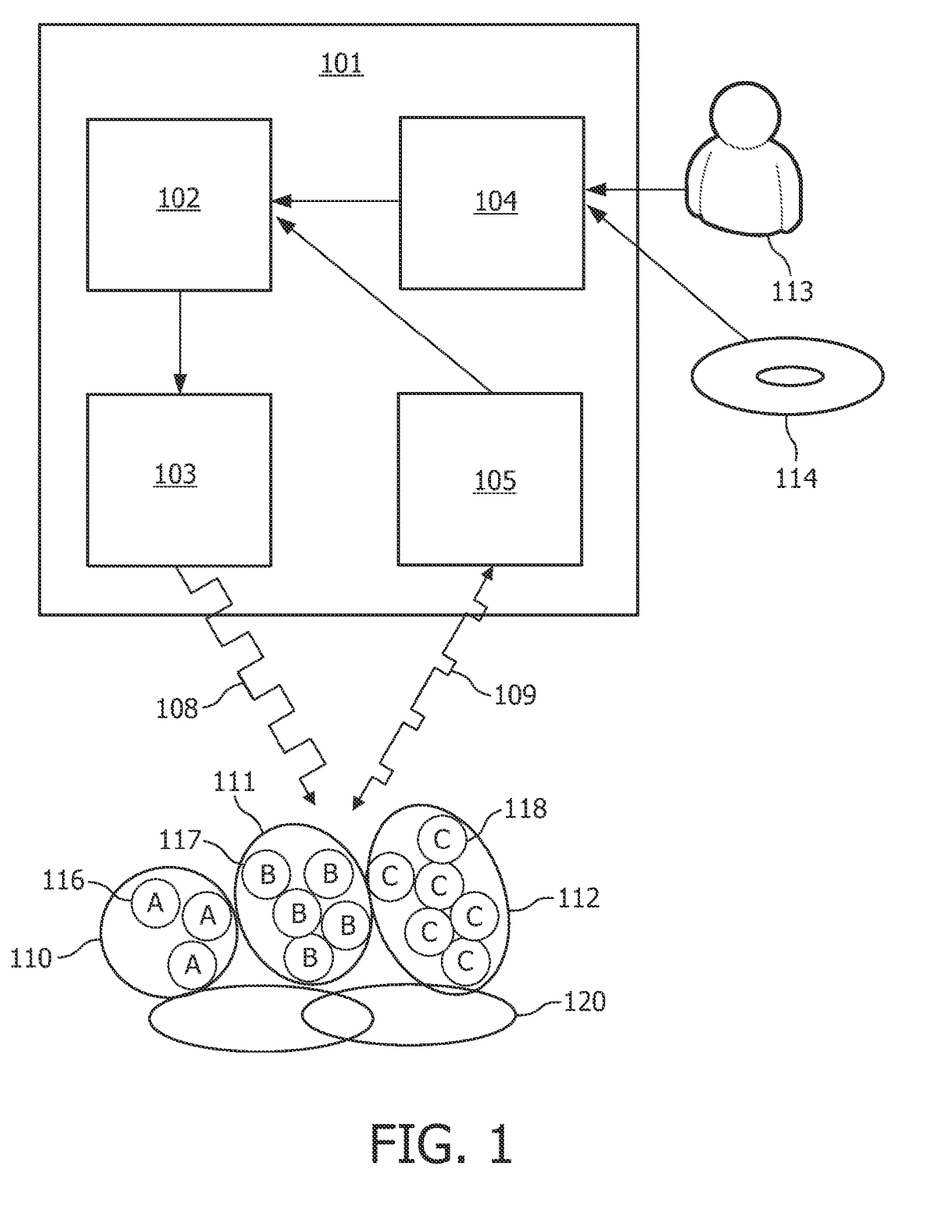
FIG. 1 shows an apparatus according to the present invention for controlling a release of a material carried by ultrasound sensitive particles.

FIG. 1 shows an apparatus 101 according to the present invention for controlling release of a material carried by ultrasound sensitive particles 116-118 comprising a control unit 102 and an ultrasound transducer 103 coupled to the control unit 102. In response to a control signal from the control unit 102, the ultrasound transducer 103 irradiates the ultrasound sensitive particles 116-118 with an ultrasonic pulse 108 having acoustic properties selected so as to interact with the ultrasound sensitive particles and thus causing the release of the material. The ultrasound sensitive particles are divided into sub-groups 110-112 of ultrasound sensitive particles, each of the sub-groups 110-112 having their respective acoustic property. As illustrated graphically here the number of sub-groups is three, where the ultrasound sensitive particles within the same sub-group are marked with the letters "A", "B" and "C".

The material according to the present invention may be an in-organic such as silicon based nanomachines, or organic material or biological material selected from pharmaceutical material, proteins, deoxyribonucleic acid (DNA), ribonucleic acid (RNA), small interfering ribonucleic acid (siRNA) and the like. The material within the microbubble or particulate delivery agent can be thought of as "instructions" to the cell to perform a function such as manufacture of a protein or suppression of a particular protein or metabolic pathway. Accordingly, by incorporating multiple "instructions" onto different sets of microbubbles, each with its own activation condition, it is possible to design a "program" consisting of a complex set of instructions that can be "executed" using ultrasound with both spatial and temporal control.

The apparatus may be applied in cell culture, in vitro, in vivo or in cell culture such as for medical or non-medical treatment.

In response to a control signal from the control unit 102 the ultrasound transducer 103 emits a sound wave of a particular acoustic property selected such that it interacts with a particular group 110-112 of ultrasound sensitive particles (USP) 116-118. The interaction causes that the ultrasound sensitive particles within this particular group become activated which causes a release of the material carried by the ultrasound sensitive particles 116-118 within this particular group. As an example, the acoustic property of the ultrasonic pulse 108 may the frequency of the pulse 108 and the properties of the different groups may be different resonance frequencies. Thus, the control signal from the control unit 102 may be to tune the frequency of the ultrasound transducer 103 to a frequency that corresponds to a resonance frequency of a particular group, e.g. group B. Instead of using the resonance frequency as a property, the property may as well be the duration of the (duty cycle) of the ultrasonic pulse or the pressure amplitude.

Accordingly, the process described here above may be considered as bio-computation where the ultrasound acoustic properties and ultrasound sensitive particles may be thought as computing instructions, wherein the software and the biochemical particles (BCP) material may be thought of as "data". By delivery of ultrasound pulses for activating and thus releasing the BCP material using the ultrasound sensitive particles is thus the enabling hardware. The bio-computing consists therefore of activating different ultrasound sensitive particles with the delivery of ultrasound pulses.

Begin Example:
Input
Instructions: encoded as combined effect of the ultrasonic pulse having acoustic properties as to interact with the ultrasound sensitive particles: frequency (F), duty cycle (D), pressure amplitude (P), waveform (W), location (L), USP particles. An "instruction" is the quadruple: I=(F, D, P, W, L, USP).
Data: Biochemical payload, BCP. For a give bioparticle there is a range of USPs that can carry the load or can be in the close proximity of the BCP.
Output
Output: Reading the output is performed using the imaging apparatus which is part of the whole ultrasound biocomputing system. The reading could be using ultrasound imaging modality as well as optical imaging modality. One possibility is to have a fluorescently tagged molecule that is activated as part of a reporter construct.

This method creates an artificial genetic construct that couples the regulatory region of a transcript of interest to the coding sequence of a light-excitable bioluminescent (fluorescent) protein. They "report on" or act as a proxy for the expression of the transcript whose regulatory region has been fused to the DNA sequence coding for the fluorescent protein. The transcript abundance of a particular gene can be indirectly inferred because the amount of protein product is understood to be indicative of transcript abundance. If there are more transcripts then there is more protein which results in more fluorescence. By measuring the intensity of the fluorescence after excitation with the appropriate wavelength of light we have readable (in imaging sense) data that reflects how the native gene would behave under the conditions within the cell.

Programming Constructs
Starting Statement
This is the execution of the first instruction in the set of programming instructions. In many cases specific starting instruction are not required.
One possibility is to have a specific initializing statement. The goal is the release of the facilitation of the first set of BCP type of particles via executing a (F, D, P, W, L, USP) that verifies that the system is operational.
Assignment Statement
Single release of ultrasound pulse at particular (F, D, P, W, L, USP) that causes release and activation of BCP is therefore is equivalent to a basic "assignment statement" of the form "A=value". In this case F stands for particular frequency, D stands for duty cycle, P stands for amplitude pressure, W stands for a particular waveform, L stands for location where the ultrasound is going to be delivered, and USP stands for ultrasound sensitive particles—specific molecular species.

Conditional Statement
The conditional statement has the generic form of:
if (A) then
perform (B)
else
perform (C)
end
Here the conditional statement A could be a releasing of a BCP which is inducing a biological response where a reporting molecule is activated and available for a read-out. Conditional statement A could consist of a reporter gene to assay for the expression of the gene of interest (for example ErbB2). One would want to obtain an in vivo diagnosis of ErbB2 positive patients instead of taking biopsy and performing fluorescent in situ hybridization and separately taking ultrasound imaging diagnostic test of the breast.
A construct is used that is directly attached to the gene of interest to create a gene fusion: GFP+ErbB2. The fused genes are going to be under the same promoter and are transcribed together. The product is a single polypeptide chain. It is preferred that both proteins are properly translated and form proteins that fold properly into active conformations. It is also assumed that both proteins will be active and dock with their substrates even though they are part of the fusion protein. In our case, when building the DNA construct a segment of DNA is inserted that codes for a flexible polypeptide linker region between the GFP and ErbB2. In this manner the reporter (GFP) and the gene product (ErbB2) will interact in a minimal way.
Conditional statement A is executed, then upon reading the outcome of the GFP reporter construct it will be known whether ErbB2 is overabundant. It is known that the growth promoting signals from ErbB2 are constitutively transmitted—promoting invasion, survival and angiogenesis of cells. If yes, then statement B is executed: the payload for B-BCP species is released. The payload could be a drug that counteracts over expression of ErbB2: Trastuzumab, also known under the trade name Herceptin (a well known breast cancer drug). This is a humanized monoclonal antibody that acts on the HER2/neu (erbB2) receptor. Else, a generic drug is released via activation of statement C. It is important to know whether herceptin should be release or another drug because it is a very expensive drug and only about 30% of the patients respond to it.
Looping Constructs
While loop: The statement of the form:
while (D)
perform (E)
end
This type of statement can be given as multiple ultrasonic pulses executing the E statement(s) until the readout of the instructions (statement D) evaluates to true.
One example is executing type of instructions in E which correspond to administer delivery of a particular drug until the diagnostic molecule is present (i.e. D evaluates to true).
Stopping Construct
It is important to have an instruction that will stop any type of computation and abort the overall execution of the program—if certain readout is indicating that proceeding is not producing the intended results. This instruction can be executed with a particular (F, D, P, W, L, USP) in combination with a biochemical particles that act in a ubiquitous manner.
End Example In one embodiment, the apparatus 101 further comprises input means 104 and imaging means 105. The input means 104 may comprise means for receiving commands from a user 113 relating to e.g. desired spatial delivery zones and the type of material to be released at the desired spatial delivery zones 120. This may be done via e.g. keyboard commands, or via mouse commands, or via a speech recognition system, or the like. The input means 104 may also comprise a disk drive, hard disk and the like having stored therein a software code or receiving pro-programmed instructions 114 from e.g. a CD disc for instructing the control unit 102 to carry out the releasing of the material at various spatial zones. These instructions may e.g. include the amount of material to be delivered to a given spatial location, the mix of different material to be given at a given location etc.

These commands codes are then implemented as control commands to the control unit 102. The imaging means 105 is used to detect the spatial distribution of the ultrasound sensitive particles, wherein the detection may be based on the use of lower mechanical index (low pressure) ultrasound. These spatial data will be used as input data for the control unit 102 in order to provide a convincing controlling, i.e. to know whether the ultrasound sensitive particles 116-118 are located at said given location 120. Thus, if the commands from a user say the material B carried by group B (ultrasound sensitive particles B) is to be released at zone X and subsequently material A carried by group A (ultrasound sensitive particles A), the imaging means 105 will initially detect whether the ultrasound sensitive particles of these two groups are located at zone X 120 using a unique signal 109. If the answer is yes, the ultrasound transducer 103 irradiates the ultrasound sensitive particles located near zone X 120 with an ultrasonic pulse that has e.g. frequency that corresponds (or within a narrow frequency interval) to the resonance frequency of group B, and after e.g. all the material A has been released, the control unit 102 instructs the ultrasound transducer 103 to tune its frequency to a frequency that corresponds to the resonance frequency of group A. Clearly, this requires that the ultrasound sensitive particles within the different sub-groups have been constructed with pre-defined properties such that e.g. the ultrasound sensitive particles within group A have "property A" (e.g. resonance frequency within a given frequency range that is preferably narrow), ultrasound sensitive particles within group B have "property B" etc.

In one embodiment, the imaging means 105 continuously monitors whether the commands have been followed. Referring to the example here above, the imaging means 105 will monitor whether all the ultrasound sensitive particles within group B have been dissolved (assuming the commands stated that all the particles B at delivery zone X are to be dissolved). It is not until the data from the imaging means (Im_M) 105 say that all the ultrasound sensitive particles within group B have been dissolved that the control unit instructs the ultrasound transducer 103 to tune its frequency to a frequency that corresponds to the resonance frequency of group A.

Figure 2:
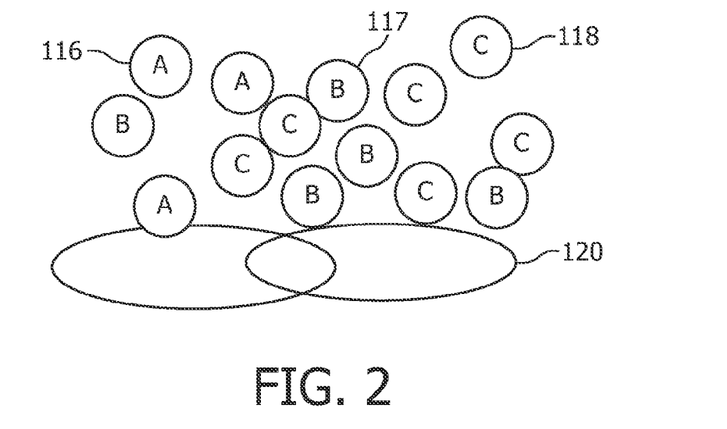
FIGS. 2-4 depict the scenario where commands received by a user include delivering the material carried by the ultrasound sensitive particles to a tissue or a cell, FIG. 5 (a) and (b) show mono-dispersed microbubbles detected in a scanning electron micrograph and measured with a particle sizer.
Figure 3:
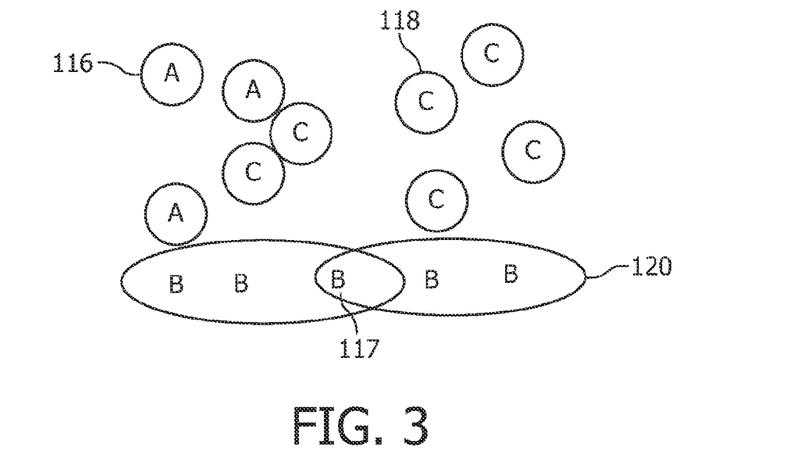
Figure 4:
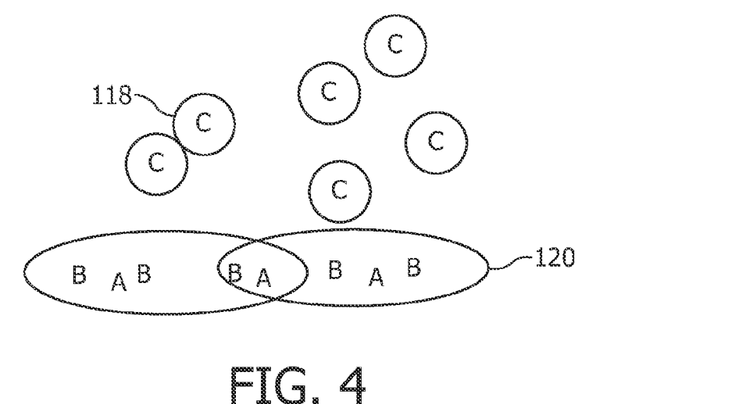

FIGS. 2-4 depict the scenario addressed here above where the commands include delivering the material such as a tissue or a cell 120. FIG. 2 shows where three groups are located near the tissue/cell 120, FIG. 3 shows where material carried by group B has been delivered to the tissue, and FIG. 4 shows where subsequently material carried by group A has been delivered to the tissue.

The ultrasound sensitive particles may be mono-dispersed microbubbles. The advantages of using such particles are that they can be made with an extremely narrow size distribution (Shi W T, Böhmer M, de Winter S, Steenbakkers J, Emmer M, van Wamel A, de Jong N, Hall C S. Ultrasonic characterization of novel monodispersed contrast agents. Proceedings of 2006 IEEE Ultrasonics Symposium. pp 301-304 (Session 2D-5).

Figure 5A:
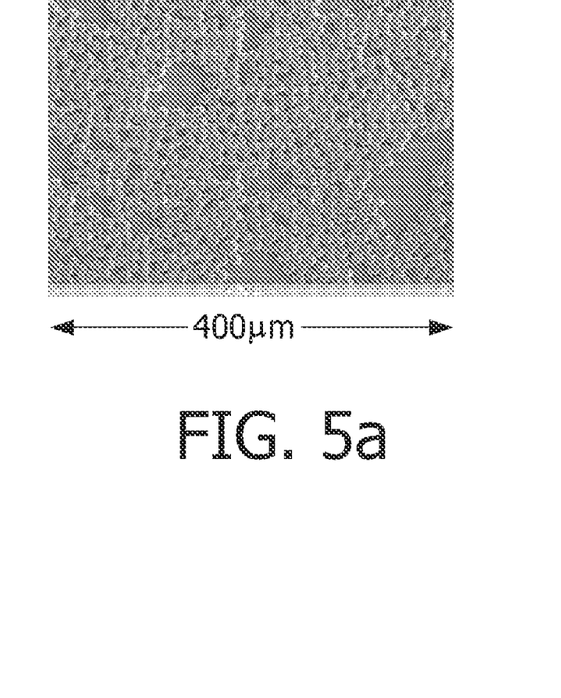
Figure 5B:
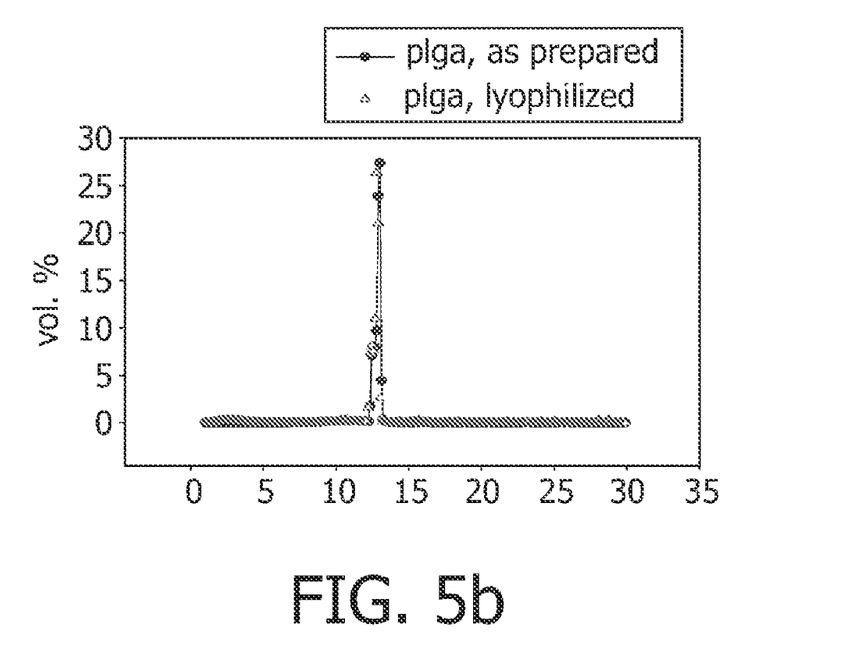

FIGS. 5 *a* and *b* show mono-dispersed microbubbles detected in a scanning electron micrograph (FIG. 5 *a*) and measured with a particle sizer (FIG. 5 *b*) where the x-axis indicates the particle diameter. Two different preparations of microbubbles are shown, plga microbubble that are prepared using the methodology described in the reference by Shi WT et al as well as a similar population of microbubbles that have been freeze-dried (lyophilized) and reconstituted in solution. Accordingly, the particle diameter or the particles in FIG. 5 (*a*) is around 12-13 μm. This mono-dispersity leads to that the population of the microbubbles resonate over narrow frequency range. Thus, by producing different groups having different sizes, it is possible to define said sub-groups having different properties, namely in this particular case having different resonance frequencies. A second advantage is the careful control over the shell thickness of the microbubbles. By carefully controlling the size distribution and having specified amount of shell material, it is possible to control the shell thickness and makeup to a very tight tolerance (see Shi WT et al.) The thickness of the shell then controls the threshold of external applied pressure where the entire population of microbubbles transitions sharply from stable to destruction (i.e. release of the material).

Figure 6:
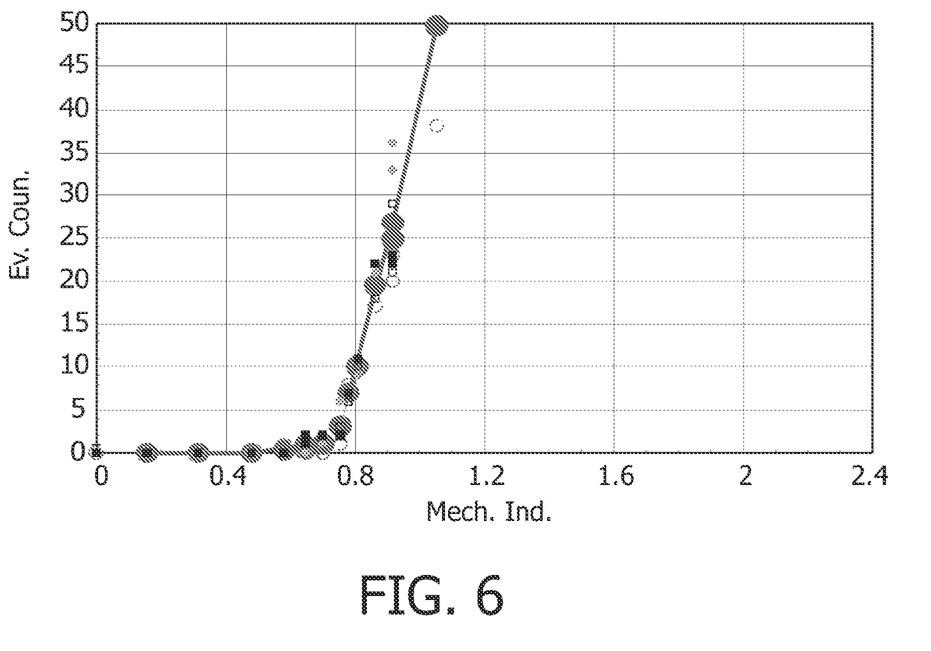
FIG. 6 shows the number of microbubbles destroyed as a function of ultrasonic pressure amplitude.

FIG. 6 shows the number of microbubbles destroyed as a function of ultrasonic pressure amplitude (x-axis is the mechanical index of the pulse and y-axis is the event count). As shown here, the microbubbles show a sharp transition at a specific pressure.

Figure 7:
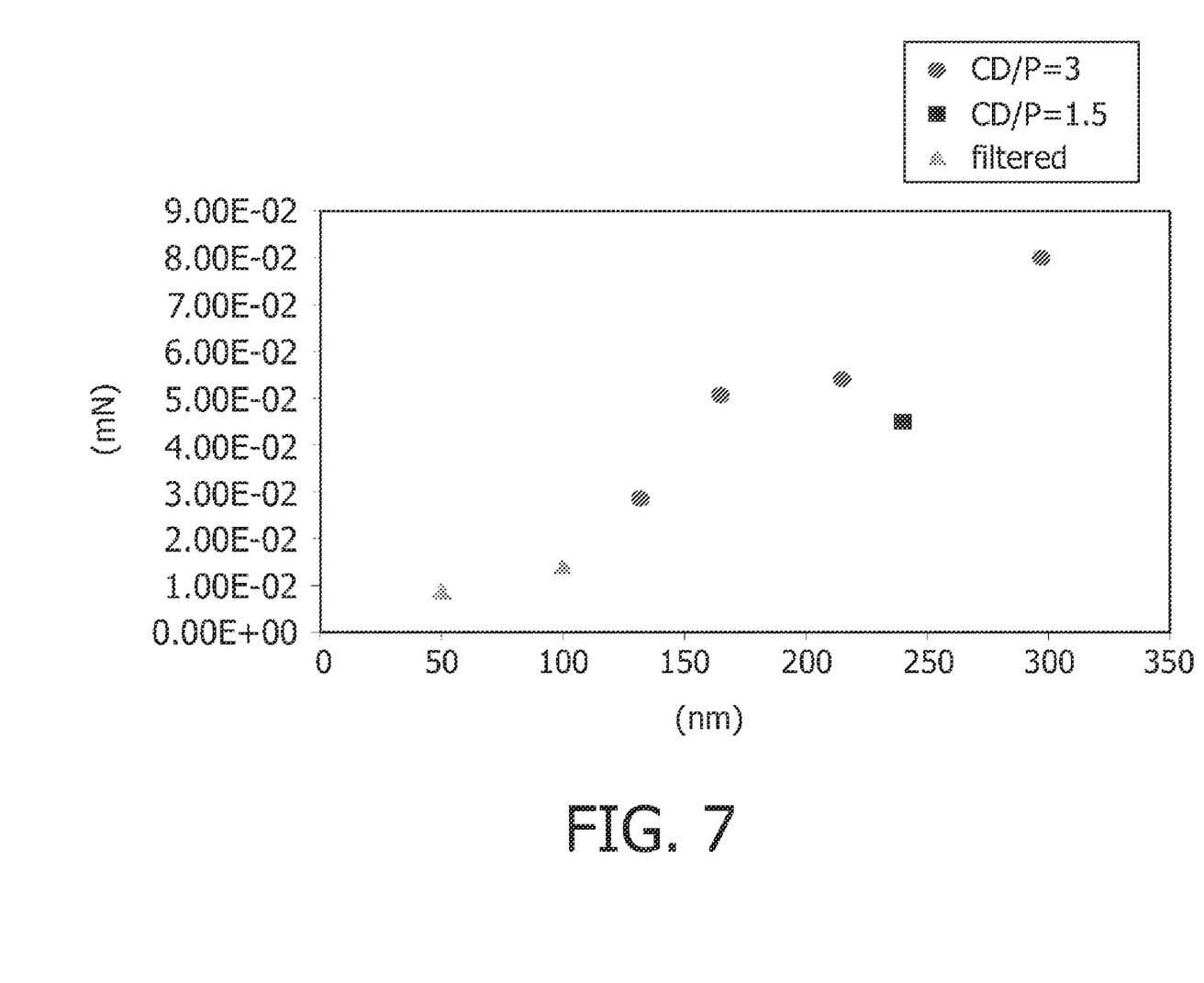
FIG. 7 shows the force needed to "destroy" and deliver the payload for three different sub-populations.

FIG. 7 shows the force needed to "destroy" and deliver the payload for three different sub-populations (one is marked with circles, one is marked with triangles and one is marked with squares) of microbubbles as a function of the thickness of the surrounding shell. Notice by careful selection of the shell thickness, discrete ultrasonic pressure fields can be chosen to deliver the payload. Accordingly, the destruction of the microbubbles can then be used to deliver any associated drug or genetic material as an example to a particular delivery zone, e.g. a tissue. Thus, ultrasound can be used to administer time-varying pressure field to the sub-groups of microbubbles to control the designated spatial and temporal delivery of any attached therapy as an example.

Figure 8:
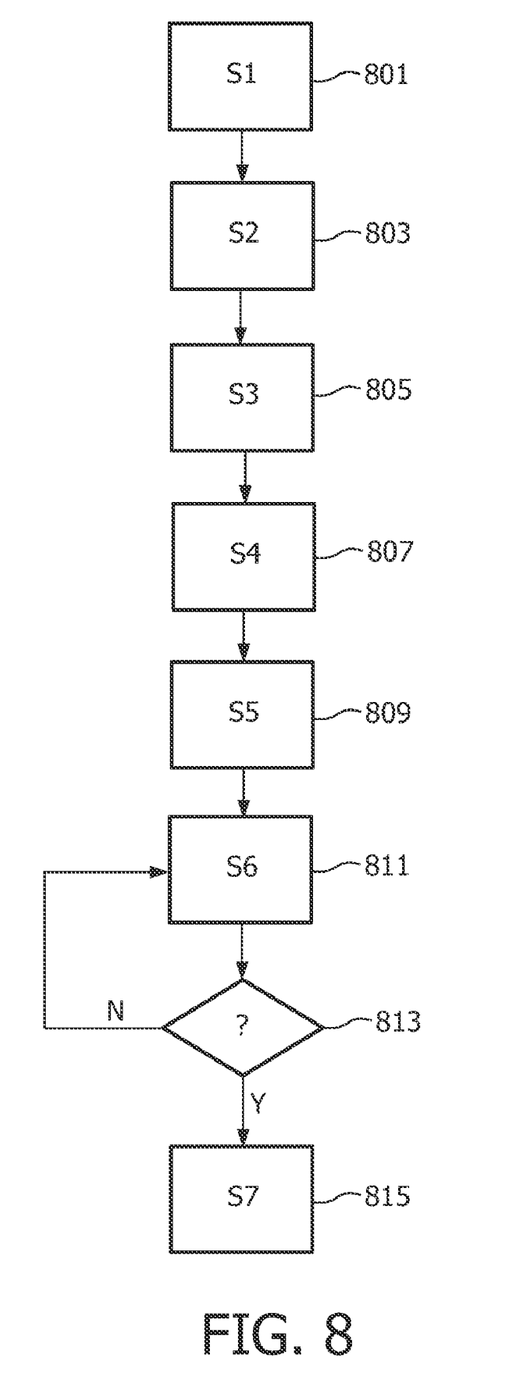
FIG. 8 shows a flow chart of one embodiment of a method according to the present invention.

FIG. 8 shows a flow chart of one embodiment of a method according to the present invention.

In this embodiment, steps (S1) 801-(S2) 803 may be considered as preparing the sub-groups of ultrasound sensitive particles, wherein step (S1) 801 relates to providing said sub-groups of ultrasound sensitive particles wherein the particles within the same sub-group preferably share a common acoustic property, step (S2) 803 relates to "attaching" or "incorporating" the material to the ultrasound sensitive particles preferably such that the particles within the same sub-group carry the same type of material. In one embodiment, the ultrasound sensitive particles are microbubbles having a shell structure, where the physical property of the microbubbles is selected from the shell thickness, the shell size, the diameter of the shell, geometrical shape of the shell, the number density of particles, and a combination thereof. The ultrasound sensitive particles may also be selected from nanoparticles, liposomes, heat shock proteins and the like. The material carried by ultrasound sensitive particles may a biological material selected from a pharmaceutical material, proteins, deoxyribonucleic acid (DNA), ribonucleic acid (RNA), small interfering ribonucleic acid (siRNA) and a combination thereof. Other materials may include artificial constructs such as nanoparticles, nanostructures, or autonomous or guided nanomachines.

In one embodiment, the respective acoustic activation property of the ultrasound sensitive particles within the same sub-group is a common resonance frequency or resonance frequency range. Thus, the acoustic activation properties of the ultrasound sensitive particles at a specific frequency or limited frequency range correspond to instruction codes that can be given according to a pre-specified "program". There is a defined grammar that encapsulates the syntax and the semantics of this programming paradigm. In a programming language syntax refers to the ways symbols may be combined to create well-formed program. Syntax provides a structural description of the various expressions that make up proper instructions. In this particular case syntax will refer to the proper formation of the instructions through predefined properties of the ultrasound sensitive particles and the properties of the ultrasonic pulse. Semantics describes the behavior of the computer when executing a program. This behavior can be described by the relationship between the input and output of a program and we will provide an example further in the text.

In step (S3) 805 the ultrasound sensitive particles are administered either together or in subsequent administration e.g. via intra-venous or arterial injection in case the method is used in-vivo.

In steps (S4) 807 commands are received from a user indicating at least one spatial delivery zone and the type of material to be released at the at least one spatial delivery zone.

In step (S5) 809 the spatial distribution of the ultrasound sensitive particles is imaged. When the imaging data indicate that the ultrasound sensitive particles are localized nearby the spatial delivery zone, the ultrasound sensitive particles are be radiated in accordance to the received commands (S6) 811.

Iteration 813 is performed wherein the imaging is utilized to check whether the commands have been completed. The imaging apparatus could receive image from ultrasound as well as from optical reading as in the case of optoacoustic imaging. As an example, if the user commands state that material B is to be delivered to a target tissue at a given delivery zone, and subsequently material A (see FIGS. 2-4), the imaging will show whether there are still some ultrasound sensitive particles comprising material B left. If there are some left, step (S6) 811 is repeated, otherwise the first set of commands have be completed (S7) 815, and the subsequent set of the received commands is performed, e.g. delivering material A to the target zone (see also FIG. 4).

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the scope of this invention. Further, in this context, and for the purposes of brevity and clarity, detailed descriptions of well-known apparatuses, circuits and methodologies have been omitted so as to avoid unnecessary detail and possible confusion.

Reference signs are included in the claims, however, the inclusion of the reference signs is only for clarity reasons and should not be construed as limiting the scope of the claims.

The invention claimed is:

1. A method of controlling release of materials carried by ultrasound sensitive particles, the method comprising:
    irradiating a plurality of sub-groups of ultrasound sensitive particles with an ultrasonic pulse having an acoustic property selected so as to interact with ultrasound sensitive particles within one sub-group of the plurality of sub-groups, and thus causing release of material carried by the ultrasound sensitive particles of the one sub-group, while avoiding release of material carried by ultrasound sensitive particles within at least one other sub-group of the plurality of sub-groups,
    wherein the ultrasound sensitive particles within the one sub-group have an acoustic activation property different from a corresponding acoustic activation property of the ultrasound sensitive particles within the at least one other sub-group, causing each respective sub-group to interact independently with the ultrasonic pulse.

2. A method according to claim 1, wherein the ultrasound sensitive particles within the one sub-group carry the same type of material, and
    wherein the ultrasound sensitive particles within the at least one other sub-group carry the same type of material, which is different from the type of material carried by the ultrasound sensitive articles within the one sub-group.

3. A method according to claim 1, wherein the ultrasound sensitive particles comprise microbubbles containing the material therein.

4. A method according to claim 1, wherein the ultrasound sensitive particles comprise microbubbles having corresponding shell structures containing the material therein.

5. A method according to claim 4, wherein the shell structure of each of the ultrasound sensitive particles within the same sub-group has a physical property characteristic for the respective acoustic activation property.

6. A method according to claim 5, wherein the physical property is selected from:
    shell thickness,
    shell size,
    diameter of the shell,
    geometrical shape of the shell,
    over or under filling of gas in the microbubbles,
    quantity of therapeutic or inert material relative to the number of microbubbles,
    chemical composition of the shell,
    number density of the ultrasound sensitive particles, and
    a combination thereof.

7. A method according to claim 1, wherein the ultrasound sensitive particles are selected from:
    microbubbles having a shell structure containing material therein,
    microbubbles containing material therein,
    microbubbles in a solution containing material therein,
    nanoparticles,
    liposomes,
    heat shock proteins, and
    a combination thereof.

8. A method according to claim 1, wherein the material carried by each of the ultrasound sensitive particles is a biological material and is selected from:
    pharmaceutical material,
    polysaccharides,
    fatty acids,
    steroids,
    proteins,
    enzymes,
    deoxyribonucleic acid (DNA),
    ribonucleic acid (RNA),
    small interfering ribonucleic acid (siRNA),
    inorganic artificial constructs,
    nanoparticles,
    nanomachines, chemicals intended to alter composition or geometry of existing sub-groups of particles,
biochemical particles, and
a combination thereof.

9. A method according to claim 1, wherein the respective acoustic activation property of the ultrasound sensitive particles within the same sub-group is a common resonance frequency or resonance frequency range.

10. A method according to claim 1, wherein the acoustic property of the ultrasonic pulse is selected from:
a frequency corresponding to a resonance frequency of the one sub-group,
pressure amplitude of the ultrasonic pulse,
duration of the ultrasonic pulse,
an arbitrary waveform, and
a combination thereof.

11. A method according to claim 1, wherein the release of the material is carried out locally in or nearby a target tissue or cell by releasing the material from the one sub-group.

12. A method according to claim 1, wherein the method is performed in-vivo or in cell culture, the method further comprising:
a. receiving at least one command indicating at least one spatial delivery zone, each command indicating at least one type of material to be released at specific ratios;
b. imaging spatial distribution of the ultrasound sensitive particles, the imaging resulting in data indicting the spatial distribution of the ultrasound sensitive particles, and in response to the spatial data;
c. irradiating the ultrasound sensitive particles in the at least one delivery zone with the ultrasonic pulse, the acoustic property of the ultrasonic pulse being controlled such that the release of the material in the at least one delivery zone is in accordance to the at least one received command; and
d. repeating steps b)-c) for each subsequent command until the received commands have been completed.

13. A method according to claim 12, wherein the at least one command further includes information about the amount of material to be delivered at the at least one spatial delivery zone or the mix of material to be delivered at the at least one spatial delivery zone or the material to be released in order to modify the acoustic activation properties of the remaining ultrasound sensitive particles.

14. An apparatus for controlling a release of a material carried by ultrasound sensitive particles included in a plurality of sub-groups, the apparatus comprising:
a control unit adapted to provide a control signal; and
an ultrasound transducer coupled to the control unit and adapted to irradiate, in response to the control signal from the control unit, the ultrasound sensitive particles with an ultrasonic pulse having acoustic properties selected so as to interact with the ultrasound sensitive particles in at least one sub-group and thus causing release of material carried by the ultrasound sensitive particles in the at least one of sub-group, while not causing release of material carried by the ultrasound sensitive particles in at least one other sub-group,
wherein the ultrasound sensitive particles in each of the sub-groups have the same acoustic activation property, different from an acoustic activation property of the ultrasound sensitive particles in at least one other sub-group.

15. An apparatus according to claim 14, further comprising:
input means for receiving instructions indicating at least one spatial delivery zone and the type of material to be released at the at least one spatial delivery zone.

16. An apparatus according to claim 15, further comprising:
imaging means, coupled to the control unit, for imaging spatial distribution of the ultrasound sensitive particles and providing spatial data indicting the spatial distribution of the ultrasound sensitive particles, wherein in response to the spatial data the control unit instructs the ultrasound transducer to irradiate the ultrasound sensitive particles localized nearby the at least one spatial delivery zone with the ultrasonic pulse, the acoustic property of the ultrasonic pulse being controlled such that the release of the material at the at least one spatial delivery zone is in accordance to the received instructions.

17. A delivery agent responsive to irradiation by an ultrasonic pulse, the delivery agent comprising:
a plurality of first ultrasound sensitive particles in a first sub-group of a plurality of sub-groups in the delivery agent, each of the first ultrasound sensitive particles carrying material and having a common first acoustic property; and
a plurality of second ultrasound sensitive particles in a second sub-group of the plurality of sub-groups in the delivery agent, each of the second ultrasound sensitive particles carrying material and having a common second acoustic property that is different from the first acoustic property,
wherein release of the material carried by the first ultrasound sensitive particles or the second ultrasound sensitive particles is controllable by selection of an acoustic property of the ultrasonic pulse with which one of the first acoustic property of the first ultrasound sensitive particles and the second acoustic property of the second ultrasound sensitive particles interacts.

18. The delivery agent according to claim 17, wherein the diameter of each of the first and second ultrasound sensitive particles is less than about 100 nm.

19. The delivery agent according to claim 17, wherein the first ultrasound sensitive particles within the first subgroup carry the same type of material, and the second ultrasound sensitive particles within the second subgroup carry the same type of material, different than the type of material carried by the first ultrasound sensitive particles.

20. The delivery agent according to claim 17, wherein each of the first and second ultrasound sensitive particles comprises a microbubble.

* * * * *